United States Patent [19]

Cunningham

[11] Patent Number: 5,792,110

[45] Date of Patent: Aug. 11, 1998

[54] SYSTEMS AND METHODS FOR DELIVERING THERAPEUTIC AGENTS TO SELECTED SITES IN A SUBJECT

[76] Inventor: Miles G. Cunningham, 28 Harvard St., Unit 2, Charlestown, Mass. 02129

[21] Appl. No.: 673,734

[22] Filed: Jun. 26, 1996

[51] Int. Cl.⁶ .................................................. A61M 5/178
[52] U.S. Cl. .......................... 604/158; 604/164; 604/890.1
[58] Field of Search .................................. 604/890.1, 164, 604/158, 95, 264, 273, 289; 128/657, 658

[56] References Cited

U.S. PATENT DOCUMENTS

| | | | |
|---|---|---|---|
| 4,243,050 | 1/1981 | Littleford | 607/122 |
| 4,518,383 | 5/1985 | Evans | 604/164 |
| 4,578,061 | 3/1986 | Lemelson | 604/164 |
| 4,581,019 | 4/1986 | Curelaru et al. | 604/164 |
| 4,769,005 | 9/1988 | Ginsburg et al. | 0604/164 X |
| 4,846,799 | 7/1989 | Tanaka et al. | 604/158 |
| 5,004,457 | 4/1991 | Wyatt et al. | 604/158 |
| 5,006,122 | 4/1991 | Wyatt et al. | 606/130 |
| 5,106,627 | 4/1992 | Aebischer et al. | 604/890.1 X |
| 5,156,844 | 10/1992 | Aebischer et al. | 604/890.1 X |
| 5,182,111 | 1/1993 | Aebischer et al. | 604/890.1 X |
| 5,306,239 | 4/1994 | Gurmarnik et al. | 604/158 |
| 5,480,389 | 1/1996 | McWha et al. | 604/158 |
| 5,487,739 | 1/1996 | Aebischer et al. | 604/890.1 |
| 5,554,148 | 9/1996 | Aebischer et al. | 604/890.1 |

OTHER PUBLICATIONS

Freeman, T. et al., "Bilateral Fetal Nigral Transplantation into the Postcommissural Putamen in Parkinson's Disease," *Annals of Neurology*, vol. 38, No. 3, 379–388 (1995).

Kordower, J. et al., "Neuropathological Evidence of Graft Survival and Striatal Reinnervation After the Transplantation of Fetal Mesencephalic Tissue in a Patient with Parkinson's Disease," *The New England Journal of Medicine*, vol. 332, No. 17, 1118–1124 (1995).

Widner, H. et al., "Bilateral Fetal Mesencephalic Gafting in Two Patients with Parkinsonism Induced by 1-Methyl-4-Phenyl-1,2,3,6-Tetrahydropyridine (MPTP)," *The New England Journal of Medicine*, vol. 327, No. 22, 1556–1563 (1992).

Brecknell, J.E. and Fawcett, J.W. (Jan. 1996) Exp. Neurol. 138:338–343.

*Primary Examiner*—Sam Rimell
*Assistant Examiner*—Robert V. Racunas
*Attorney, Agent, or Firm*—Jean M. Silveri

[57] ABSTRACT

Systems for delivering a therapeutic agent to a selected site in a subject are disclosed. These systems enable precise placement of selected amounts, e.g., very small amounts, of a therapeutic agent to a predetermined site or sites in a three dimensional array in a subject with minimal trauma to the subject. These delivery systems include a guide cannula for penetrating a selected site in a subject to a predetermined depth and a delivery cannula for delivering the therapeutic agent to the subject. The guide cannula has an axial bore extending therethrough with an open proximal end and an opening at a distal portion thereof. The delivery cannula has an axial bore extending therethrough, a flexible distal end portion, and an outer diameter which is less than the inner diameter of the guide cannula. Methods of delivering therapeutic agents to selected sites in a subject using these delivery systems are also described.

34 Claims, 7 Drawing Sheets

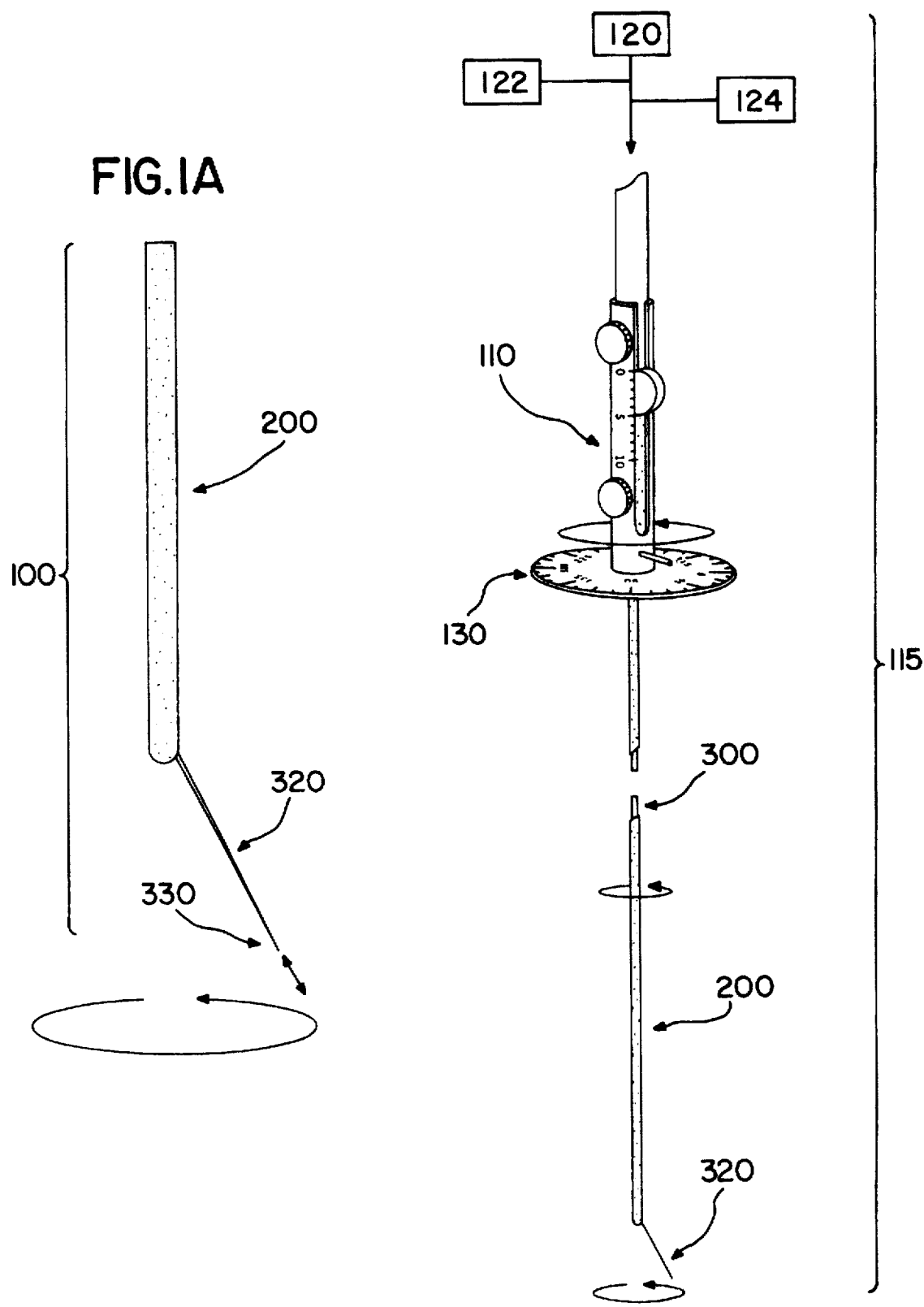

FIG. 2A
FIG. 2C
FIG. 2D
FIG. 2B
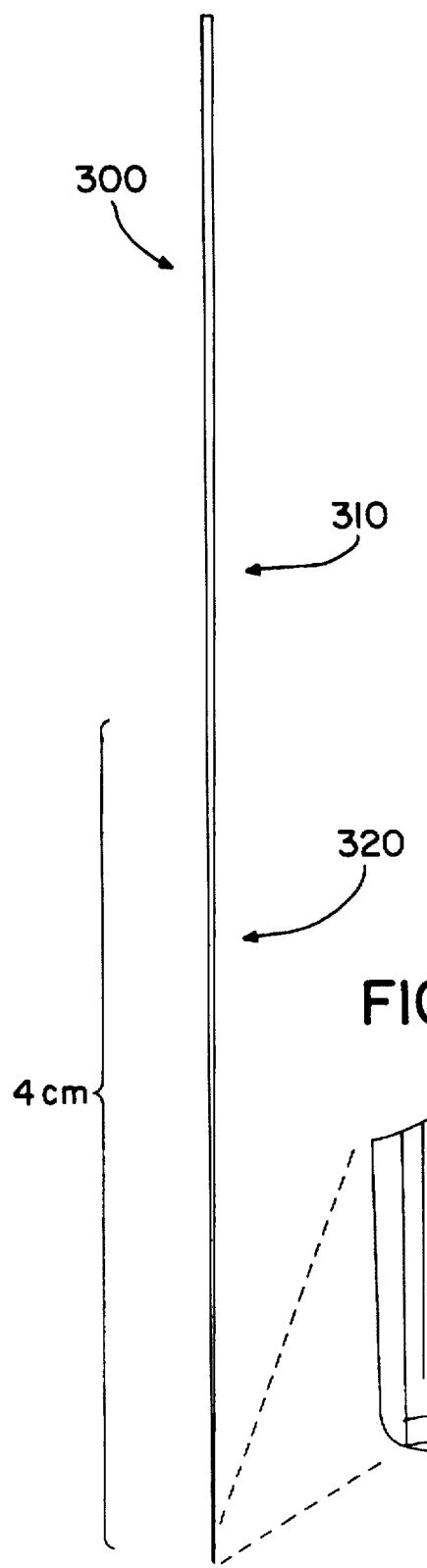
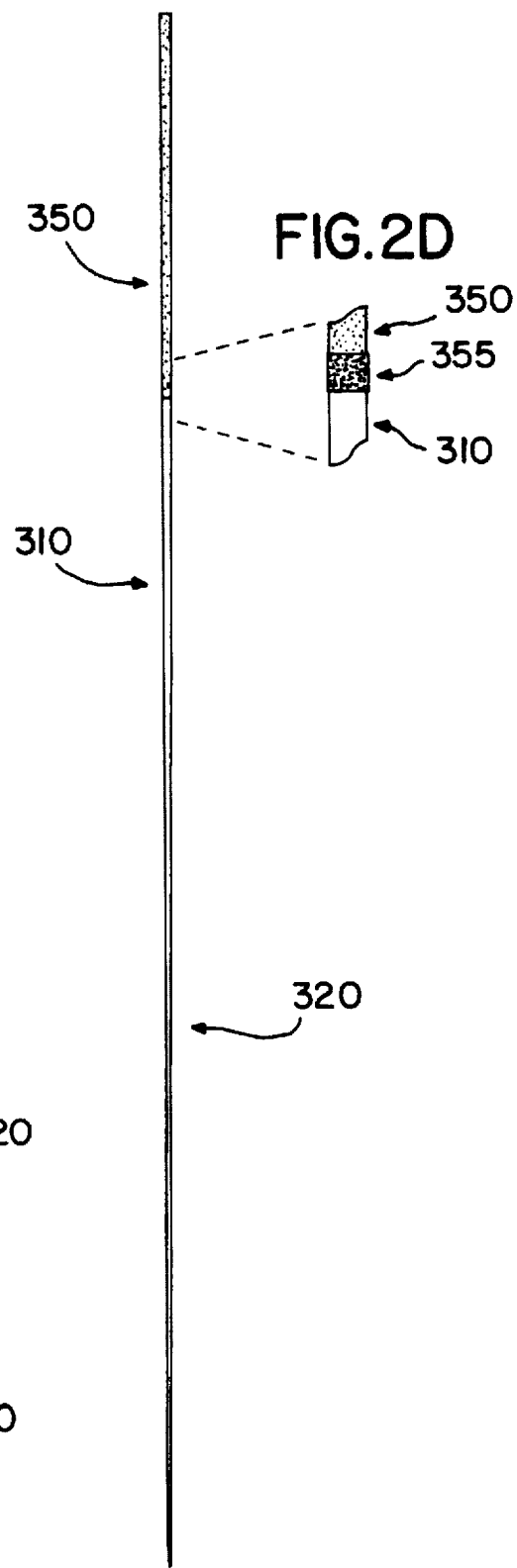

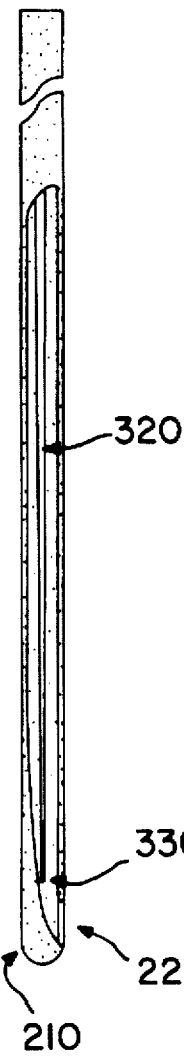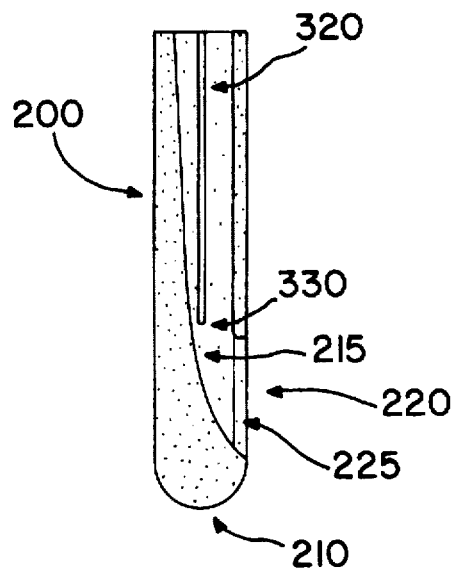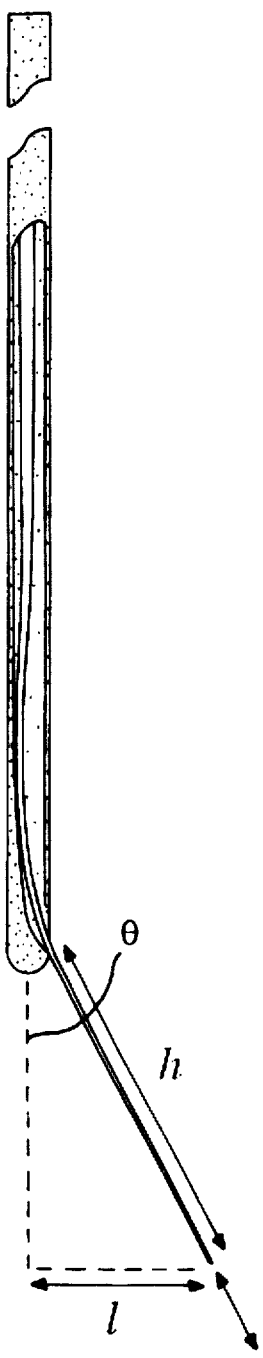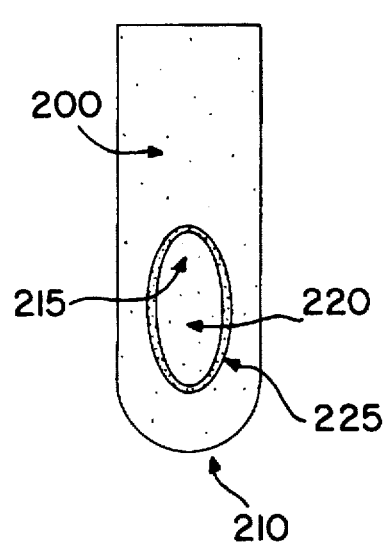

SYSTEMS AND METHODS FOR DELIVERING THERAPEUTIC AGENTS TO SELECTED SITES IN A SUBJECT

BACKGROUND OF THE INVENTION

The invention relates to systems and methods for delivering a therapeutic agent to a selected site in a subject. These systems and methods allow for precise placement of selected amounts, e.g., very small amounts, of a therapeutic agent at a predetermined site in a subject with minimal trauma to the subject. In addition, if the therapeutic agent to be delivered to the subject includes cells or tissue, the systems and methods of the invention provide for increased survival of the cells or tissue in the subject. The systems and methods of the invention can also be used to remove, with great precision and minimal trauma to a subject, selected substances, cells, and/or tissues from a selected site in a subject. One area in which use of the systems and methods of the invention is particularly relevant is in cell and/or tissue, e.g., neural cell and/or neural tissue, transplantation.

Neural transplantation holds promise as a method of reconstituting cell populations, supplementing levels of certain brain chemicals, and reestablishing neural circuitry. Presently, one main technique or a variation thereof is used for transplanting neural tissue. See e.g., Kordower, J. H. et al. (1995) *N. Engl. J Med.* 332(17):1118–1124; Freeman, T. et al. (1995) *Annals Neurol.* 38(3):379–388; Widner, H. et al. (1992) *N. Engl. J. Med.* 327(22):1556–1563. This technique employs a cell or tissue delivery device which includes a stereotaxic needle with a blunt end and a tip diameter from about 0.9 to about 1.5 mm. The cells or tissue to be transplanted are loaded into this needle, the needle is advanced toward the transplant site, and the cells or tissue are released from the needle at the site. Using this needle, multiple grafts can be placed along a straight path. However, if one wishes to graft at a site which is not along this path, the needle must be removed and reinserted along a new path. Reinsertion of this needle causes additional trauma to the tissue in the path of the needle. Typically, it is desirable to make multiple grafts along different paths. In such a case, the needle is generally removed and reinserted into the subject from about six to about eight times per side of the brain, increasing trauma to the brain tissues with each new penetration.

In addition to the simple injection needles described above, other instruments have been described for transplantation of tissue into the brain. See U.S. Pat. Nos. 5,006,122 and 5,004,457. U.S. Pat. No. 5,006,122 discloses a brain tissue transplantation method utilizing a cannula within a cannula assembly. The first cannula is a large bore cannula which is fixed to a stereotaxic holding apparatus and which is advanced into the brain to the transplant site. The second cannula, which carries donor tissue and a stylet which is used to expel the tissue from the second cannula, is guided within the lumen of the first cannula to the transplant site. The tissue is then transplanted into the brain by withdrawing the first and second cannulas while the stylet within the second cannula is maintained in a fixed position. The stylet is later removed, leaving only the transplanted tissue in the recipient.

These instruments have in common a number of disadvantages. For example, the diameters of the instruments are relatively large, e.g., 0.9 mm or greater. The use of large diameter transplant instruments to deliver therapeutic agents decreases precision in placement of the injection while increasing trauma and disruption of the graft microenvironment. For example, it has been shown that insertion of a cannula into the brain during standard neural transplant procedures causes localized trauma to the tissue, destruction of neurons, and damage to the blood brain barrier (Perry, V. H. et al. (1993) *TINS* 16(7):268–273). This damage in turn results in several undesirable events such as macrophage, T-cell, and blood-derived IgG infiltration to the transplant site. Furthermore, reactive gliosis mounts and production of neurite inhibitory factors (e.g., chondroitin-6-sulfate and cytotactin/tenascin) is upregulated resulting in the formation of a glial scar that hinders neurite outgrowth (McKeon, R. J. et al. (1991) *J Neurosci.* 11:3398–3411). These processes, which occur on the cellular and molecular level within the graft's microenvironment, ultimately result in cell death and poor graft integration.

In addition, these instruments do not provide for reliable delivery of very small volumes to a selected site in a subject. Small volumes of fluid injected from these instruments tends to adhere to the relatively large surface area of the cannula and can flow up around the outside wall of the guide cannula. Furthermore, as the large caliber instrument is withdrawn, a greater suction is produced. The suction created by removal of these instruments pulls extruded cell suspension into the tract of the cannula, thereby removing cells from the transplant site and resulting in decreased precision in placement of transplants. Furthermore, when these instruments are used for transplantation, transplants can be placed only along a single tract, each tract requiring removal and repenetration of the instrument into the brain. Therefore, the brain must be entered many times in order to place transplants in a three dimensional configuration. These multiple penetrations or insertions cause further trauma to the brain of the transplant recipient. Thus, the disadvantages inherent in the structure of these instruments contribute to low (5–10% of transplanted cells) and variable graft survival and graft-induced functional recovery of the graft in the recipient. These suboptimal techniques remain the state of the art in neural transplantation.

Thus, there is a need for an instrument which can be used to precisely deliver any volume of a therapeutic agent, e.g., a factor, a compound, a chemical, cells, etc. to a selected site in a subject, e.g., a human, in a manner which incurs an absolute minimum level of tissue damage and which is capable of disseminating numerous grafts in a three dimensional configuration. Such an instrument would improve graft survival and functional integration of the graft in the subject leading to further improvement in the quality of life for the subject.

SUMMARY OF THE INVENTION

The invention features systems (hereinafter "delivery systems" "delivery instruments" or "delivery apparatuses or devices") and methods for delivering a therapeutic agent to a selected site, e.g., a desired location, in a subject. These systems and methods meet the above-cited needs by allowing for precise placement of selected amounts, e.g., very small or large amounts, of a therapeutic agent to a predetermined site in a subject with minimal trauma to the subject. Use of the systems and methods of the invention to deliver a therapeutic agent to a subject results in a level of tissue damage which is substantially less than that caused by known delivery devices. Moreover, the systems and methods of the invention can be used to disseminate numerous grafts in a three dimensional configuration within a subject with only a minimal number of penetrations into the subject. In addition, if the therapeutic agent to be delivered to the subject includes cells or tissue, the systems and methods of the invention provide for increased survival of the cells or tissue in the subject. The systems and methods of the invention can also be used to remove, with great precision and minimal trauma to a subject, selected substances, cells, and/or tissues from a selected site in the subject.

Accordingly, the invention features a system for delivering a therapeutic agent to a selected site in a subject which includes a guide cannula for penetrating a selected site in a subject to a predetermined depth and a delivery cannula for delivering the therapeutic agent to the subject. The guide cannula has an axial bore extending therethrough which has an open proximal end and an opening at a distal portion thereof. The delivery cannula has an axial bore extending therethrough, a flexible distal end portion, and an outer diameter which is less than the inner diameter of the guide cannula. The shape of the delivery cannula enables the delivery cannula to be inserted within the bore of the guide cannula and also allows for movement of the delivery cannula along the bore of the guide cannula. The delivery cannula can be manufactured of an inert, e.g., nontoxic and nonreactive with host tissue and components thereof, material which can be formed into various shapes and sizes with selected specifications and which is flexible. As used herein, the term "flexible" refers to at least a portion, e.g., a distal portion, of the delivery cannula of the invention which is capable of being deformed or bent without breaking. The flexible portion of the delivery cannula is capable of returning to its original position or form upon removal of a force which causes it to deform or bend. Typically, at least a portion of the delivery cannula can be deflected at an angle from the guide cannula to deliver the therapeutic agent to a selected site in a subject. The flexibility of the delivery cannula allows for placement of a therapeutic agent in a three dimensional array in a subject with minimal trauma to the subject. Preferably, the material from which the delivery cannula is produced is flexible or pliable when formed into cannulas having very small diameters at their distal ends, e.g., from about 1 to about 200 micrometers, preferably from about 10 to about 190 micrometers, more preferably from about 20 to about 180 micrometers, yet more preferably from about 30 to about 170 micrometers, still more preferably from about 40 to about 160 micrometers, and most preferably from about 50 to about 100 to about 150 micrometers. The material can be manufactured from a variety of materials such as glass, polymeric materials such as polycarbonate, polypropylene, and metals such as stainless steel. In a preferred embodiment, the delivery cannula is manufactured of a glass such as borosilicate or pyrex. In an alternative embodiment, the delivery cannula can be manufactured from more than one, e.g., a combination of the materials described herein. For example, the delivery cannula can be composed at its distal portion of the flexible material described herein and at its proximal portion of a more rigid material such as a metal, e.g., stainless steel. The guide cannula is typically produced from an inert material which provides sufficient rigidity to stabilize the delivery cannula in the subject, e.g., which is stiff or rigid to such a degree as to be able to penetrate the subject such that at least its distal portion is adjacent to or in proximity to a selected site in the subject. For example, the materials from which the guide cannula can be produced include materials such as metals, e.g., stainless steel, gold, and gold alloy. In addition, the guide cannula can be manufactured from a combination of such materials.

In a preferred embodiment, the distal end of the guide cannula is a blunt end which minimizes damage to the tissue of the subject upon insertion of the guide cannula into the subject. The distal opening of the guide cannula can be disposed at the distal end of the guide cannula, coaxial with the lumen thereof, or it can be a side wall mounted opening disposed in a side wall of the guide cannula. If the opening at the distal portion of the guide cannula is a side wall mounted opening disposed in a side wall, the side wall of the guide cannula opposite the side wall mounted opening increases in thickness distally to converge with a distal aspect of the side wall mounted opening.

In one embodiment, the delivery cannula tapers from a point or location, e.g., a proximal portion, which is a selected distance from the distal end to form a tube having a diameter at its distal end which is smaller than the diameter at its proximal end. Preferably, the delivery cannula tapers such that the distal end of the delivery cannula is at least about ten fold, preferably at least about 20 fold, more preferably at least about 50 fold, and most preferably at least about 100 fold or more smaller than the diameter of the proximal end of the delivery cannula. In one embodiment, the guide cannula has a diameter of about 0.5 millimeters to about 3 millimeters and the delivery cannula tapers from a point or location which is a selected distance from the distal end to a distal end to form a tube having a diameter at its distal end of about 1 micrometer to about 200 micrometers.

The systems of the invention can further include or comprise means for moving the delivery cannula relative to the guide cannula, means for moving the guide cannula relative to the selected site in the subject, means for aspirating and expelling the contents of the delivery cannula, means for supplementing the contents, e.g., therapeutic agent, of the delivery cannula while it remains in the subject, e.g., in the tissue of the subject, during a surgical procedure, means for recording electrophyisological events at the selected site in the subject, and/or means for transmitting selected wavelengths of light to the distal portion of the delivery cannula. In one embodiment, components of a stereotaxic apparatus provide the means for moving the delivery cannula relative to the guide cannula, the means for moving the guide cannula relative to the selected site in the subject, and the means for aspirating and expelling the contents of the delivery cannula.

Therapeutic agents which can be delivered to a subject using the systems and the methods of the invention include agents which have a therapeutic effect, e.g., reduce or eliminate deleterious symptoms or undesirable effects caused by, for example, disease or injury, and/or which preserve health, on a subject. The therapeutic agents can be delivered alone or in combination with a pharmaceutically acceptable carrier or diluent through the diameter of the delivery cannula to the selected site in the subject. Pharmaceutically acceptable carriers or diluents are art recognized formulations and include saline, aqueous buffer solutions, solvents and/or dispersion media. The use of such carriers and diluents is well known in the art. These carriers or diluents are preferably sterile and fluid to the extent that easy syringability exists. Preferably, the solution is stable under the conditions of manufacture and storage and preserved against the contaminating action of microorganisms. Such therapeutic agents include cells, e.g., neural cells such as mesencephalic cells and striatal cells, and tissues, growth factors, e.g., neurotrophic factors, e.g., ciliary neurotrophic factor for treatment of amyotrophic lateral sclerosis, brain-derived neurotrophic factor for treatment of Parkinson's disease, glial growth factors for treatment of multiple sclerosis and Parkinson's disease, and nerve growth factor for treatment of Alzheimer's disease. These growth factors can be delivered to a subject together with cells or tissues using the delivery systems of the invention. The cells delivered to the subject using the delivery systems of the invention can be obtained from any source, e.g., mammals such as pigs, rodents, and primates e.g., humans and monkeys.

Other examples of therapeutic agents include chemotherapeutic agents which cross the blood brain barrier such as carmustine and chemotherapeutic agents which do not cross the blood brain barrier such as cisplatin, photodynamic drugs or agents such as porphyrin analogues or derivatives, and antimicrobial agents such as antibiotics. In one embodiment, the delivery systems of the invention can be used to deliver concentrated doses of chemotherapeutic agents directly to brain tumors, e.g., brain carcinomas, thereby bypassing systemic administration and its accompanying undesirable side effects. Similarly, the delivery systems of the invention can be used to deliver antibiotics to focal infectious processes in the brain of a subject, e.g., brain abscesses. Selected concentrations of these antibiotics can be locally administered using these systems without the limitation of the antibiotic's ability to cross the blood brain barrier. Photodynamic drugs or agents can be locally administered using the delivery systems of the invention, allowed to accumulate in precancerous or cancerous cells, and subsequently illuminated by light transmitted through he delivery cannula. Illumination of the cells containing the photodynamic drugs activates he drug which in turn results in destruction of the precancerous or cancerous cells.

Other therapeutic agents which are used to treat acute events such as trauma and cerebral ischemia, or agents which can be used to treat chronic pathological processes can also be delivered by employing the delivery systems of the invention. Examples of these agents include nitric oxide synthase inhibitors and superoxide dismutase to inhibit oxidative stress caused by trauma, ischemia, and neurodegenerative disease, thrombolytics, e.g., streptokinase, urokinase, for direct dissolution of intracerebral thrombosis, and angiogenic factors to help reestablish circulation to traumatized or infarcted areas.

Still other examples of therapeutic agents which can be delivered to a subject using the delivery systems of the invention include nucleic acids, e.g., nucleic acids alone, e.g., naked DNA, and nucleic acids in delivery vehicles such as lipid delivery vehicles and viruses. For example, nucleic acids which can be delivered to a subject using the systems of the invention can encode foreign tissue antigens that cause tumors, e.g., brain carcinomas, to be attacked by the immune system. In addition, further examples of nucleic acids which can be delivered to a subject using the systems of the invention include nucleic acids which encode immunostimulators (e.g., cytokines, IL-2, IL-12, $\gamma$-interferon) to boost the immune system, nucleic acids which encode antigens which render tumor cells more vulnerable or more susceptible to chemotherapy, e.g., Allovectin-7, and nucleic acids which encode apoptotic proteins which cause the tumor cells to self-destruct. Alternatively, nucleic acids encoding neurotrophic factors, deficient proteins, specialized receptors, et cetera can also be delivered to a subject using the delivery systems of the invention.

The therapeutic agents can be chronically infused into a subject using the delivery systems of the invention. Chronic infusion can be accomplished by advancing the delivery cannula to the target site, e.g., target brain site, securing it to the surrounding bone structures, e.g., skull, with, for example, acrylic, and attaching a constant infusion device, such as a mini-osmotic pump loaded with the therapeutic agent to be infused or delivered.

In one embodiment, the delivery systems of the invention can be used to deliver neural cells to a selected site, e.g., putamen, caudate, substantia nigra, nucleus accumbens, or hippocampus, in the central nervous system. For example, when neural cells, e.g., mesencephalic cells, are transplanted into subjects having Parkinson's disease, the cells are typically delivered to the putamen and caudate nucleus. In addition, neural cells, e.g., GABAergic neurons, can be delivered using the delivery systems of the invention to epileptic foci in the brain of a subject. Furthermore, the delivery systems of the invention can be used to deliver cortical neurons, e.g., hNT neurons, to repopulate areas of neurodegeneration caused by stroke or trauma.

The invention also features methods for delivering a therapeutic agent to a selected site in a subject. Subjects who can be treated using this method include mammals, e.g., primates such as humans and monkeys, pigs, and rodents. Selected sites in a subject include locations to which it is desirable to deliver a therapeutic agent. Examples of such locations include areas of neurodegeneration in the central nervous system of a subject. These methods include the steps of inserting a guide cannula having the features described herein such that its distal portion is proximal to a selected site in the subject and inserting a delivery cannula, which releasably holds a therapeutic agent, into the guide cannula. The delivery cannula is inserted into the guide cannula a predetermined distance such that the distal end of the delivery cannula is proximal to an opening at the distal portion of the guide cannula. The methods then include the steps of extending the delivery cannula through the opening at the distal portion of the guide cannula along a first extension path to the selected site in the subject, and releasing the therapeutic agent from the delivery cannula into the selected site in the subject to form an injection site. In an alternative embodiment, the delivery cannula is inserted into the guide cannula prior to insertion of the guide cannula into the subject. In yet another alternative embodiment, the delivery cannula is loaded with the therapeutic agent to be delivered to the subject after it is inserted into the guide cannula. The delivery cannula can taper from a point or location at a selected distance from a distal end to the distal end to form a tube having a diameter at its distal end which is smaller than the diameter at its proximal end.

In another embodiment, the method further includes or comprises, after the step of releasing the therapeutic agent to the selected site, the steps of retracting the delivery cannula a predetermined distance from the first injection site, and releasing, e.g., by injection, the therapeutic agent from the delivery cannula into a second selected site in the subject to form a second injection site. These additional steps can be repeated as desired, e.g., at least twice.

In yet another embodiment, the invention further includes or comprises, after the step of releasing the therapeutic agent to the selected site or a series of sites along one path, the steps of retracting the delivery cannula such that the distal end of the delivery cannula does not extend beyond the opening at the distal portion of the guide cannula, rotating the guide cannula a predetermined angle from the first extension path of the delivery cannula, extending the delivery cannula through the opening at the distal portion of the guide cannula along a second extension path to a second selected site or series of sites in the subject, and releasing the therapeutic agent from the delivery cannula into the second selected site in the subject to form a second injection site or sites. These additional steps can also be repeated as desired, e.g., at least twice. This method results in placement of transplants in a three dimensional configuration in the subject with minimal trauma to the tissues of the subject.

BRIEF DESCRIPTION OF THE DRAWINGS

FIGS. 1A–1B depict schematic views of a delivery system of the invention. FIG. 1A is a close-up view of a delivery system in which the delivery cannula extends through a distal portion of the guide cannula. FIG. 1B is a perspective view of a delivery system together with a standard apparatus for manipulating the system.

FIGS. 2A-2D depict various delivery cannulas for use in the delivery systems of the invention. FIGS. 2A and 2B depict the distal portion of a delivery cannula of the system of the invention which is manufactured from glass. FIG. 2B is a close-up view of the tip of the delivery cannula. FIGS. 2C and 2D depict an alternative embodiment in which the proximal end of the delivery cannula is replaced with a stainless steel cannula.

FIG. 3C depicts a delivery cannula within a cut-away guide cannula.

FIGS. 4A-4D are close-up perspective views of the distal portion of delivery systems of the invention which illustrate the design of the guide cannula and the spatial relationship of the delivery cannula to the inner lumen and distal opening of the guide cannula.

FIG. 6A depicts the mechanics and geometry of the system of the invention which allow for the placement of a conical array of injections at selected sites in a subject. FIG. 6B is a two-dimensional scaled diagram of a single delivery cannula tract with 0.5 microliter injections every one millimeter along a trajectory 12 mm long at a 20° angle from the midline or central axis of the guide cannula. FIG. 6C is a scaled, three-dimensional top view of a conical array of injections that can be produced with repeated delivery cannula injection tracts as illustrated in FIG. 6B. FIG. 6D is a scaled, three-dimensional side view of a completed conical array of injections as illustrated in FIG. 6C.

DETAILED DESCRIPTION OF THE INVENTION

Figure 3A:
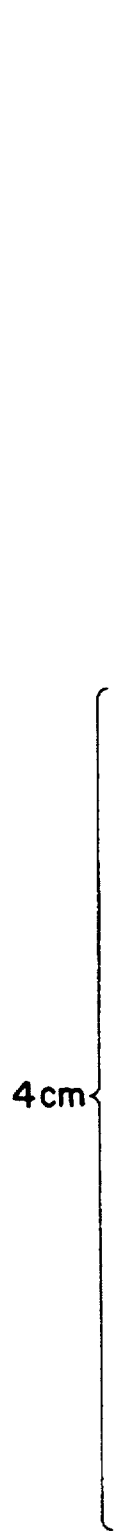
FIGS. 3A-3C depict intact and cut-away guide cannulas.

This invention is further illustrated by the following figures which in no way should be construed as being further limiting. The contents of all cited references (including literature references, issued patents, published patent applications, and co-pending patent applications) cited throughout this application are hereby expressly incorporated by reference.

FIG. 1A illustrates a preferred embodiment of a delivery system 100 of the invention. FIG. 1B illustrates a delivery system combined with an apparatus for manipulating the system 115. The delivery system together with the apparatus for manipulating the system 115 includes a small-diameter guide cannula 200, e.g., a stainless steel guide cannula, a delivery cannula 300, a configuration of instruments for precise control of cannula depth, such as the vernier guide shown 110, means for aspirating and expelling 120 precise measurable volumes of the contents of the delivery cannula, such as a stylet or hydraulic mechanism, with a means for supplementing the contents of the delivery cannula while it remains in the tissue of the subject during a surgical procedure, means for recording electrophysiological activity 122, and means for transmitting light with predetermined wavelengths through the delivery cannula 124. The manipulation system can be mounted onto a standard stereotaxic instrument. An angle dial 130 can be used for precise control of rotation of the cannulas. Light delivery systems which can be used with the systems of the invention are commercially available from, for example, QLT, Vancouver, B.C. and PDT, Inc., Santa Barbara, Calif. Stereotaxic instruments which can be used with the systems of the invention are commercially available from, for example, Radionics, Inc., Burlington, Mass., and Westco Medical Corp., San Diego, Calif. Appropriate modifications of the delivery instrument manipulating devices, injection mechanisms, electrophysiological recording equipment, light delivery systems, and stereotaxic apparatuses are within the skill of the ordinary artisan. The delivery cannula 300 can be extended from the guide cannula to form a first extension path and then withdrawn into (or retracted within) the guide cannula 200. The guide cannula can then be rotated a predetermined angle within the subject and the delivery cannula extended from the guide cannula along a second extension path which is different from the first extension path.

One embodiment of the delivery cannula of the invention is illustrated in FIGS. 2A and 2B. In these figures, the delivery cannula 300 is produced from a long tube or pipette composed of glass such as borosilicate or Pyrex with an inner diameter (i.d.) of about 0.4 mm and outer diameter (o.d.) of about 0.7 mm. Such pipettes can be custom made of a variety of different materials in addition to glass and custom made to have a wide range of diameters. Using a modified glass electrode puller equipped with a lengthened heating coil and which is designed to accommodate a 10 cm or longer glass pipette, the pipette is pulled to produce a very long (about 4 cm) gently tapering shank 320. The delivery cannula tip 330, which is illustrated in FIG. 2B, is produced by removing the distal-most portion of the pulled pipette at an appropriate distance from the distal end to produce a delivery cannula with a selected distal end diameter. Any rough or sharp edges can be eliminated, i.e., smoothed out, by, for example, fire-polishing. Delivery cannula tips can be produced with diverse diameters to suit the properties of the therapeutic agent which is to be delivered to the subject. FIGS. 2C and 2D illustrate an alternative embodiment in which a metal cannula 350 of equal o.d. as the delivery cannula, e.g., glass pipette, is substituted for at least a portion of the glass pipette and is affixed with epoxy or other suitable material 355 to the glass pipette 310 proximal to the beginning of the shank 320.

Figure 3B:
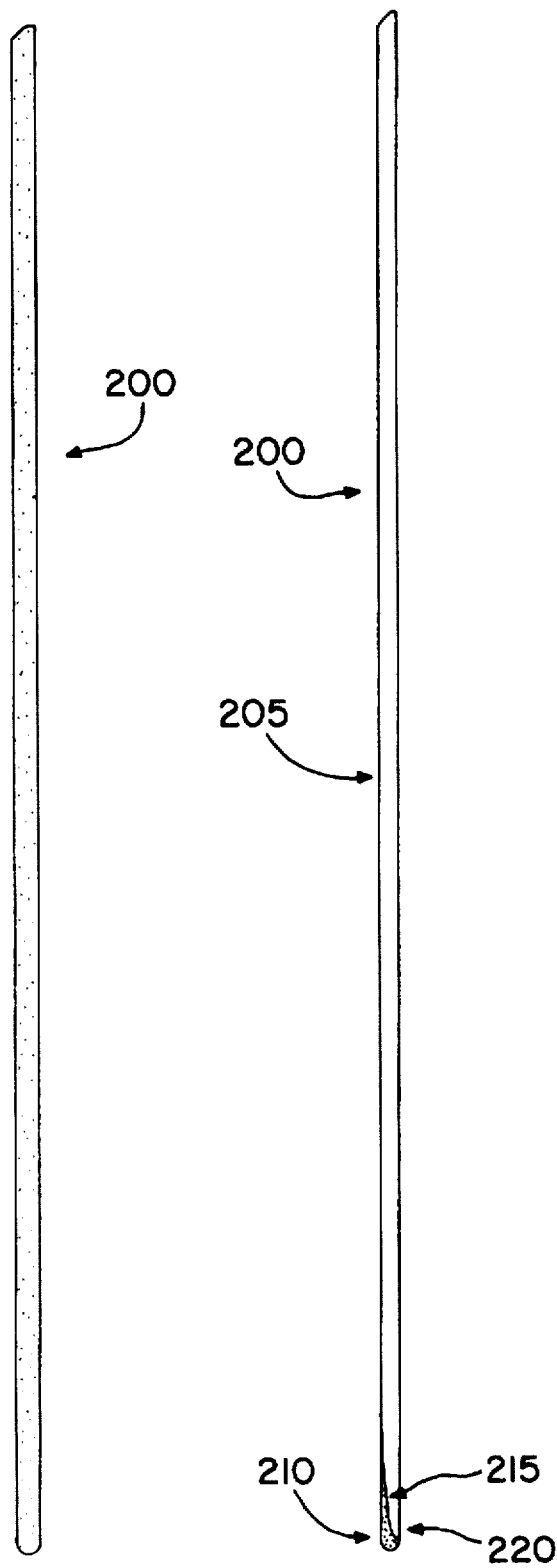
Figure 3C:
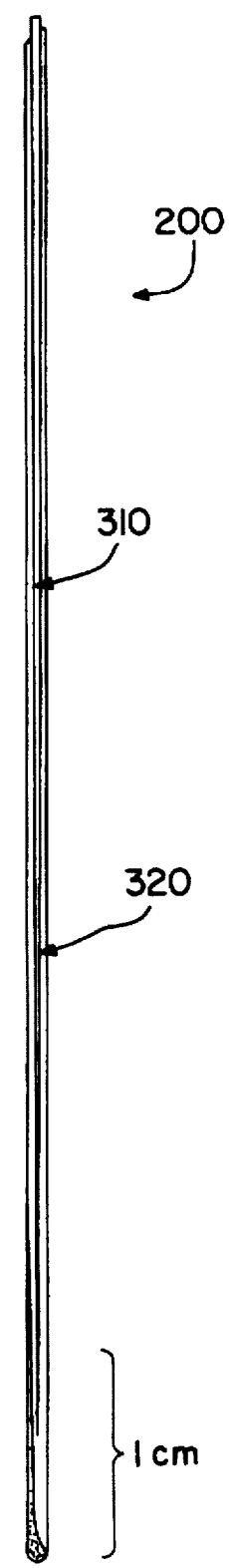

A preferred embodiment of the guide cannula is illustrated in FIGS. 3A-3C and 4A-4D. The appropriate o.d. of the guide cannula for delivery of a selected therapeutic agent to a selected site in a subject can be determined based on the following considerations: (1) the o.d. should be a diameter which renders the guide cannula sufficiently rigid such that it is insertable into a subject without deforming or bending and such that it is rotatable in a subject with minimal deviation from its central axis, e.g., evenly rotatable (does not wobble or rotate unevenly from side to side); (2) the o.d. should be minimized to the extent possible to reduce trauma to the subject upon insertion; and (3) the o.d. should be a diameter which preserves an i.d. which can accommodate a delivery cannula having a selected or desired o.d., e.g., having an i.d. sufficient to allow delivery of a selected therapeutic agent to a selected site in a subject. With reference to FIGS. 3A-3C and 4A-4D, such a guide cannula is constructed from standard 19TW stainless steel tubing, with an o.d. of about 1.07 mm and an i.d. of about 0.8 mm, which permits passage of a delivery cannula with an o.d. of about 0.7 mm. The length of the guide cannula 200 is sufficient to reach targets or selected sites in a subject at various distances with the use of a depth stop and with or without a conventional vernier guide for more precise depth placement. Referring to FIGS. 3B and 3C, the distal end 210 of the guide cannula is blunt so as to gently push tissue out of its path during penetration to thereby minimize trauma to the subject's tissue. The bore of the guide cannula 205 is centrally located within the guide cannula 200 and extends throughout the length of the guide cannula 200 along the longitudinal axis of the cannula. The diameter of the bore 205 is greater than the outer diameter of the uniform length 310 of the delivery cannula 300. If the delivery cannula is to extend from a side wall mounted opening disposed in a side wall of the guide cannula, one side of the distal inner wall of the guide cannula opposite the side wall mounted distal opening typically increases in thickness distally (for example, for a length of about 0.5 to 1.0 cm) 215 to converge with a distal aspect of the side wall mounted opening. This increase in thickness of the side wall opposite the side wall mounted distal opening of the guide cannula imposes a bend or curve in the flexible delivery cannula as the delivery cannula progresses downward within the bore of the guide cannula. This bend or curve in the delivery cannula allows the delivery cannula to exit the guide cannula through the distal opening or exit port 220 just proximal to the distal end 210 of the guide cannula. (The edges 225 of the distal opening or exit port 220 are smoothed to prevent tissue damage or coring during penetration of the guide cannula.) In this manner and as shown in FIG. 4D, the delivery cannula is diverted in a manner dependent upon the characteristics of the thickness of the side wall opposite the distal opening and other factors such as the material from which the delivery cannula is manufactured, and the shaping and taper of the shank of the delivery cannula, and exits the guide cannula at a precise angle θ, thereafter traveling along a straight trajectory. The thickness of the side wall of the guide cannula opposite the distal opening 215 as well as any of the additional factors which contribute to the diversion of the delivery cannula can be modified to increase or decrease the exit angle θ of the delivery cannula. In addition, in an alternative embodiment, a groove or channel can be machined down the thickened wall 215 of the guide cannula, preferably down the center, to more accurately guide the distal portion or tip of the delivery cannula through the guide cannula to the selected opening or exit 220 at a distal portion of the guide cannula. Use of such a groove or indentation to guide the delivery cannula through the guide cannula minimizes side-to-side movement or motion of the delivery cannula during extension and retraction within the guide cannula. Referring to FIG. 4D, given the exit angle θ and the distance h, the distance from midline l can be calculated and the final target can be precisely reached.

Figure 6A:
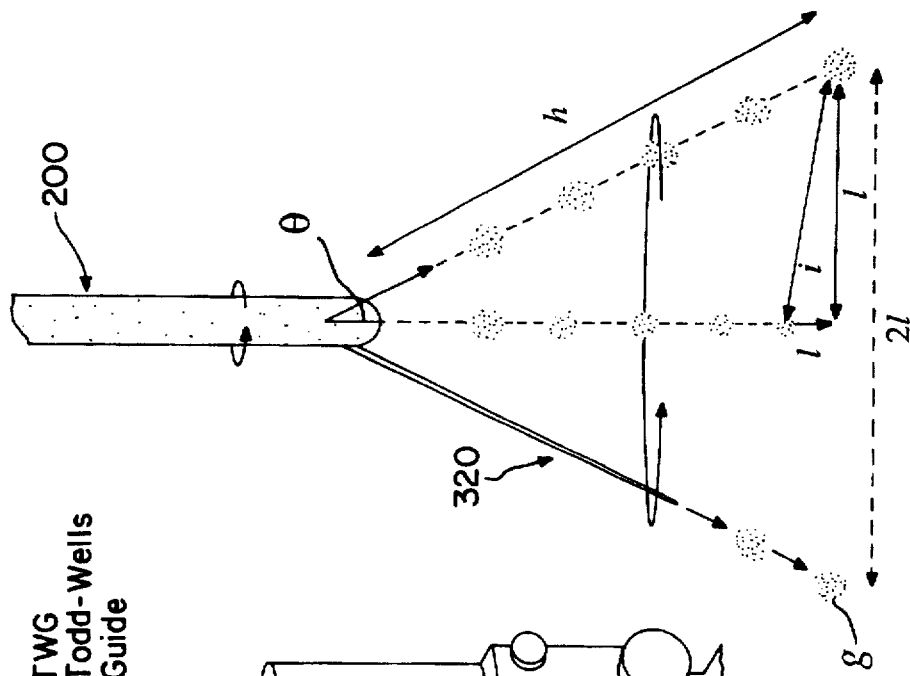
FIGS. 6A-6D depict the mechanics and geometry of a delivery system of the invention and the three dimensional array of implants which can be placed at selected sites in a subject using the system.
Figure 5:
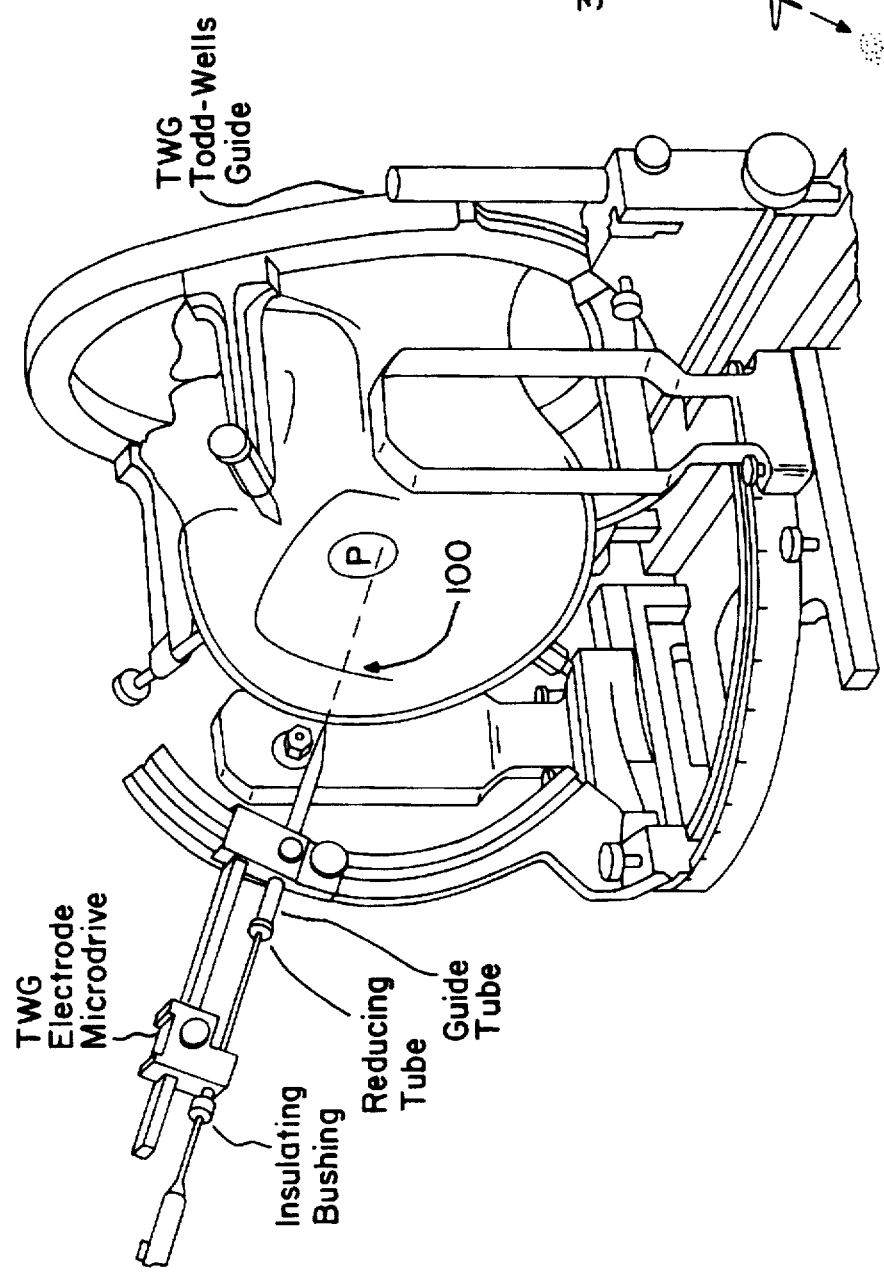
FIG. 5 depicts a diagram of a typical stereotaxic device illustrating a delivery system of the invention in use as it appears in a stereotaxic surgical procedure.

FIG. 5 depicts a stereotaxic apparatus which can be used in conjunction with a delivery system of the invention to deliver therapeutic agents to the brain, e.g., to the posterior putamen P, of a subject. These stereotaxic apparatuses are commercially available from Radionics, Burlington, Mass.. FIG. 6A illustrates the procedure for distributing multiple injections of a therapeutic agent, such as neural cell grafts g, to a subject, in a three dimensional, e.g., conical, array. The delivery cannula is extended distance h from the end of the guide cannula at angle θ to form a first extension path. The distal-most injection is thus placed at distance l from the midline of the guide cannula. The diameter of the base of the array is thus 2×l. Withdrawal of the delivery cannula into the guide cannula can be interrupted at selected distances to allow numerous injections to be made along the trajectory of the delivery cannula to form a series of injections along the first extension path. Upon withdrawal of the delivery cannula into the bore of the guide cannula such that the distal end of the delivery cannula does not extend beyond the opening at the distal portion of the guide cannula, the guide cannula is rotated a predetermined angle from the first extension path of the delivery cannula and the delivery cannula is extended or advanced again through the opening at the distal portion of the guide cannula along a second extension path thereby allowing a new series of injections. Referring to FIG. 6A, the angle of rotation of the guide cannula determines the distance i between grafts of the first delivery cannula extension path and the second delivery cannula extension path and subsequent delivery cannula extension paths.

Figure 6B:
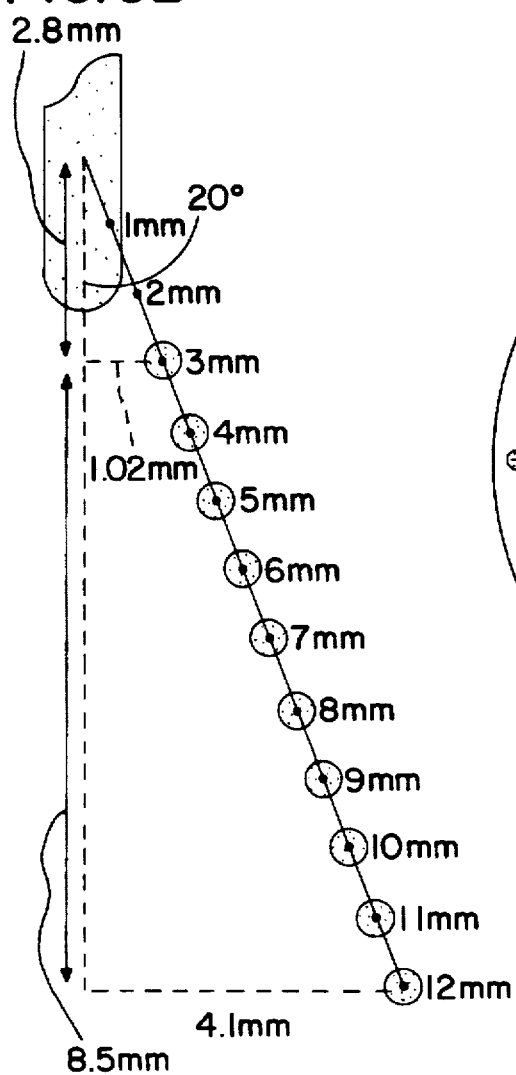
Figure 6C:
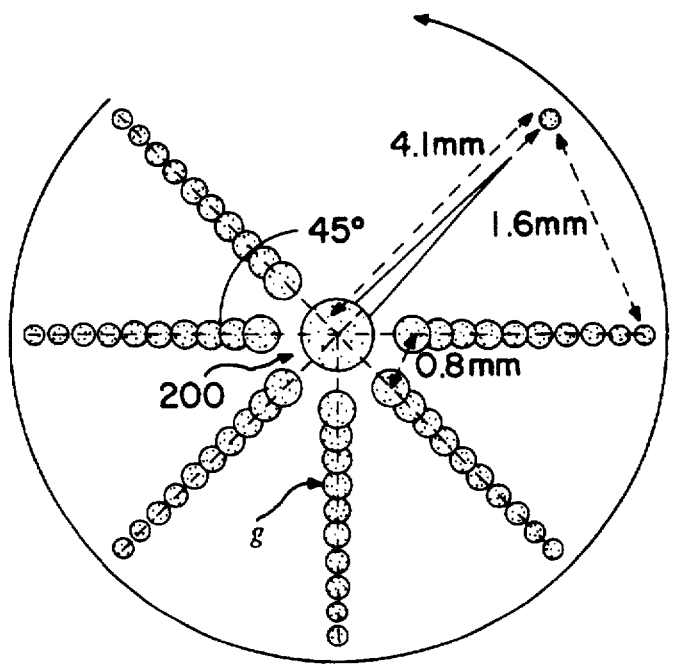
Figure 6D:
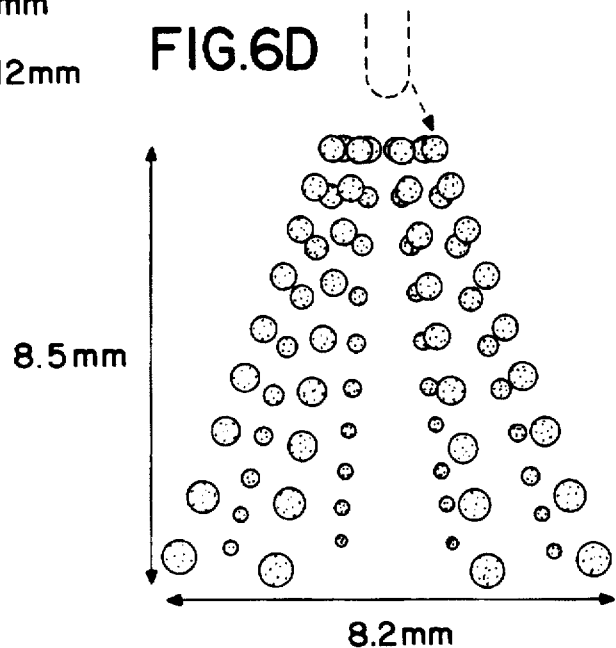

FIGS. 6B–6D are examples of scale diagrams of micrograft arrays as they appear in three-dimensional space. FIG. 6B illustrates a series of 10 implants of 0.5 microliters each which are placed 1 mm apart, along a single 12 mm delivery cannula trajectory, diverted from the guide cannula midline by 20°. If the therapeutic agent to be delivered includes cells, this implant volume need be spaced only every 0.5 mm to result in excellent survival and integration of the cells in the subject. To avoid the cellular and molecular mechanisms involved in tissue trauma and graft rejection, the implants delivered to the subject using the delivery systems of the invention are placed a selected distance from the distal end of the guide cannula, the source of the tissue trauma and the location of the deleterious cellular and molecular events contributing to graft rejection. Typically, the selected distance is about 1 mm from the distal end of the guide cannula. Thus, given the implant configuration illustrated in FIG. 6B, the graft furthest from the guide cannula is about 4.1 mm from the midline of the guide cannula, and the graft nearest the guide cannula is about 1.02 mm from the midline of the guide cannula.

FIG. 6C is a three-dimensional representation, viewed from the top, of the process of producing a micrograft array in which radial delivery cannula trajectories are at 45° angles. With this distribution, the centers of the grafts g most distal from the guide cannula are separated by about 1.6 mm, and the grafts most proximal to the guide cannula are separated by about 0.8 mm. FIG. 6D is a three-dimensional representation of the side view of a completed grafting array. The base of the conical array is about 8.2 mm across and its apex is about 1.02 mm across, while its height is about 8.5 mm. Thus, this configuration of 80 implants of 0.5 microliters each, 1 mm apart, disseminated from a single penetration of the guide cannula, allows for approximately 40 microliters of a therapeutic agent, e.g., cells, e.g., neural cells, to be implanted within a tissue volume in a subject of less than one cubic centimeter. The number of injections within a given area can be altered considerably depending on such variables as distance of delivery cannula extension, diversion angle of delivery cannula from the guide cannula, distance between injections, volume of injections, and angle of rotation between trajectories. Furthermore, these three dimensional arrays of implants can be stacked or tiered. These stacks or tiers are generated by injecting one array of implants of a therapeutic agent, withdrawing the guide cannula a selected distance, and repeating the injection procedure.

Figure 7A:
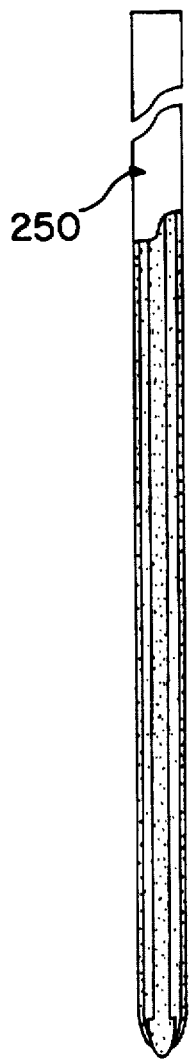
FIGS. 7A-7C depict an alternative embodiment of a delivery system of the invention in which the delivery cannula is advanced along a single trajectory and along the same axis as the guide cannula.
Figure 7B:
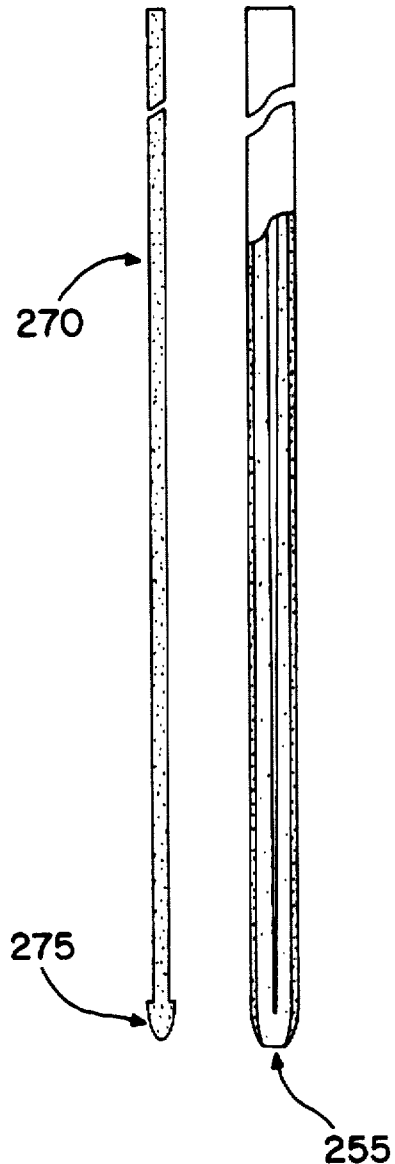
Figure 7C:
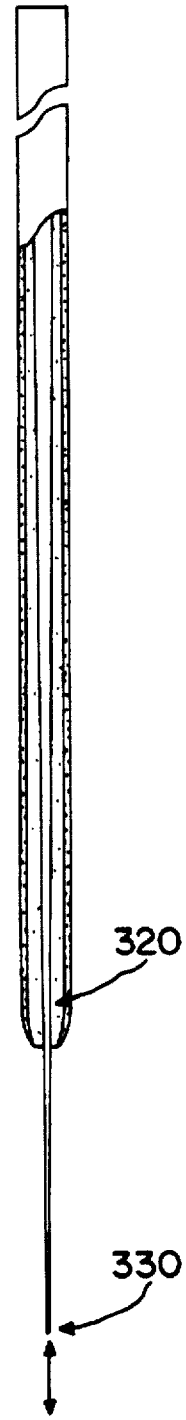

FIGS. 7A–7C illustrate an alternative embodiment in which the guide cannula 250 is similar to the guide cannula 200 described above (see FIGS. 3A–3C and 4A–4D) except the bore is uniform for the length of the guide cannula and at the distal opening or exit port 255 at the end of the guide cannula it tapers circumferentially to accommodate the fitting of the blunt tip 275 of an occluder 270. With the occluder 270 in position, as in FIG. 7A, the end of the guide cannula is thus rounded and can be advanced into the subject, e.g., into the subject's brain, with minimal trauma to a point many millimeters proximal to the target. The occluder 270 is then removed and the delivery cannula 300 as described above (FIGS. 2A–2C) is extended or advanced through the guide cannula, and the tip 330 is extended from the distal opening or exit port 255 to the target. Similar to the procedure described above, withdrawal of the delivery cannula can be interrupted at specified distances to allow multiple injections to be made along the delivery cannula's trajectory. Alternatively, this simplified embodiment is suitable for single injections or for long-term infusion.

In addition, the delivery cannula of the delivery systems of the invention can be guided through the guide cannula such that it bends and exits through an opening at the distal portion of the guide cannula at an angle to allow for approach of a selected target site while avoiding or bypassing important anatomical structures adjacent to and/or surrounding the site. Using the delivery systems of the invention, neural cells can be delivered to remote or high risk targets such as the substantia nigra with minimal inflammation and edema and with minimal risk of damaging important anatomical structures, e.g., the brain stem. Thus, the delivery systems or delivery apparatuses of the invention can be used to discretely and consistently place small volumes of a therapeutic agent at selected anatomical site(s) while preserving local cytoarchitecture. If cells are delivered using the delivery systems of the invention, cell survival in the subject can be increased two fold or more over that seen with the techniques presently used for human neural transplantation. In situations where it is desirable to use fetuses from humans or other mammals as a source of cells or tissue to be transplanted, this increase in cell survival using the delivery systems of the invention decreases the number of fetuses required to provide the same level of clinical improvement in the recipient subject. For example, if 10 fetuses from which cells are harvested for transplantation are normally required using the delivery devices in the art to produce a desired level of clinical improvement in a human, only 5 fetuses would be required using the delivery system of the invention to produce the same level of clinical improvement in a subject. The delivery systems or delivery apparatuses of the invention can also be used to deliver therapeutic agents, with minimal disruption, to spinal cord locations, peripheral nervous system locations and locations in and around, e.g., eye chambers, the eye, et cetera.

Additional applications of the delivery systems of the invention are diverse and include use in microbiopsy, electrophysiological recording, and photodynamic therapy. Just as tissue can be discretely placed in a selected site in a subject in one, two or three dimensional arrays, tissue can be removed from discrete, selected sites in a subject using the delivery systems of the invention in a one, two or three dimensional array. This is achieved by aspirating cells into the tip of the delivery cannula, or by first injecting a small volume of enzyme, such as trypsin, allowing a short incubation, and then aspirating the dissociated cells into the tip of the delivery cannula. In this embodiment, the delivery cannula becomes a removal cannula. Microbiopsies of aberrant cells, e.g., cancerous cells, using the systems of the invention can be performed with minimal trauma to the subject while reducing the risk of seeding, e.g., leaving a path of aberrant cells, normal tissue with aberrant cells. In addition, aberrant cells, e.g., cancer cells, can be removed using the systems of the invention, genetically manipulated in culture, and delivered to the subject as a vaccine with extremely high tumor specificity.

The delivery systems of the invention can also be used to record electrical, e.g., neural, activity, in a subject. For example, areas of abnormal electrical activity, e.g., epileptic foci, can be located using the systems of the invention. In this embodiment, the carrier of the therapeutic agent can include an electrolytic solution and the delivery cannula can serve as an electrode. Once the site of abnormal electrical activity is located, the therapeutic agent, can be delivered to the site also using the systems of the invention and characterized using standard electroencephalography. Moreover, because the therapeutic agent to be delivered can be in an electrolytic solution, recording and then delivery or injection can be achieved in one step.

An additional application for the delivery systems of the invention is in the field of photodynamic therapy for the destruction of cancer cells within precise foci. Photodynamic therapy is performed by injecting a photoreactive agent into a tumor site which preferentially accumulates within the tumor cells. With the delivery cannula still in position after delivery of the photoreactive agent, light is transmitted to the tip (distal portion) of the cannula (which can be designed to emit light) to thereby activate the photoreactive agent and destroy the tumor cells. Further description of methods of performing photodynamic therapy can be found in Fisher, A. M. et al. (1995) *Lasers Surg. Med.* 17(1):2–31 and Stables, G. I. et al. (1995) *Cancer Treat. Rev.* 21(4):311–323.

EQUIVALENTS

Those skilled in the art will recognize, or be able to ascertain using no more than routine experimentation, many equivalents of the specific embodiments of the invention described herein. Such equivalents are intended to be encompassed by the following claims.

I claim:

1. A system for delivering a therapeutic agent to a selected site in a subject, comprising:

a rigid guide cannula for penetrating the subject to a site adjacent to the selected site, the guide cannula having an axial bore extending therethrough within which a delivery cannula can be disposed, an open proximal end, an opening at a distal portion thereof, a distal end which is a blunt end, and a wall which is sufficiently rigid such that it is capable of deflecting, at a predetermined deflection angle relative to the midline of the guide cannula, a delivery cannula disposed therein as the delivery cannula is extended through the opening at the distal portion of the guide cannula; and a delivery cannula disposable within the guide cannula for delivering the therapeutic agent to the selected site in the subject, the delivery cannula having an axial bore extending therethrough, a flexible distal end portion, and an outer diameter which is less than the inner diameter of the guide cannula, wherein the delivery cannula, when extended through the opening at the distal portion of the guide cannula, is adapted to be deflected by a wall of the guide cannula at a predetermined deflection angle relative to the midline of the guide cannula and along a new trajectory imposed by the deflection angle and thereafter maintaining the new trajectory in the subject without being diverted by forces imposed by structures within the subject.

2. The system of claim 1, wherein the distal end of the guide cannula is a blunt end.

3. The system of claim 1, wherein the distal opening of the guide cannula is a distal opening disposed at the distal end of the guide cannula, coaxial with the lumen thereof.

4. The system of claim 1, wherein the distal opening of the guide cannula is a side wall mounted opening disposed in a side wall of the guide cannula.

5. The system of claim 1, wherein the delivery cannula tapers from a proximal end to a distal end to form a tube having a diameter at its distal end which is smaller than the diameter at its proximal end.

6. The system of claim 1, further comprising means for moving the delivery cannula relative to the guide cannula.

7. The system of claim 1, further comprising means for moving the guide cannula relative to the selected site in the subject.

8. The system of claim 1, further comprising means for aspirating and expelling the contents of the delivery cannula.

9. The system of claim 1, further comprising means for recording electrophysiological events at the selected site in the subject.

10. A system for delivering a therapeutic agent to a selected site in a subject, comprising:
  a guide cannula for penetrating the subject to a site adjacent to the selected site, the guide cannula having an axial bore extending therethrough, the guide cannula further having an open proximal end and an opening at a distal portion thereof; and
  a delivery cannula disposable within the guide cannula for delivering the therapeutic agent to the subject, the delivery cannula tapering from a proximal end to a distal end to form a tube having a diameter at its distal end which is at least five fold smaller than the diameter at its proximal end, the delivery cannula further having an axial bore extending therethrough, a flexible distal end portion, and an outer diameter which is less than the bore diameter of the guide cannula.

11. The system of claim 10, wherein the distal end of the guide cannula is a blunt end.

12. The system of claim 10, wherein the distal opening of the guide cannula is a distal opening disposed at the distal end of the guide cannula, coaxial with the bore thereof.

13. The system of claim 10, wherein the distal opening of the guide cannula is a side wall mounted opening disposed in a side wall of the guide cannula.

14. The system of claim 10, wherein the delivery cannula is manufactured of a material selected from the group consisting of glass, a polymeric material, and a metal.

15. The system of claim 10, wherein the delivery cannula is manufactured from glass.

16. A method for delivering a therapeutic agent to a selected site in a subject, comprising:
  (a) inserting a rigid guide cannula adjacent to a selected site in the subject, the guide cannula having an axial bore extending therethrough within which a delivery cannula can be disposed, an open proximal end, an opening at a distal portion thereof, a distal end which is a blunt end, and a wall which is sufficiently rigid such that it is capable of deflecting, at a predetermined deflection angle relative to the midline of the guide cannula, a delivery cannula disposed therein as the delivery cannula is extended through the opening at the distal portion of the guide cannula;
  (b) inserting a delivery cannula into the guide cannula proximal to the opening at the distal portion, the delivery cannula releasably holding the therapeutic agent and having a flexible distal end portion and an outer diameter which is less than the bore diameter of the guide cannula, wherein the delivery cannula, when extended through the opening at the distal portion of the guide cannula, is adapted to be deflected by a wall of the guide cannula at a predetermined deflection angle relative to the midline of the guide cannula and along a new trajectory imposed by the deflection angle and thereafter maintaining the new trajectory in the subject without being diverted by forces imposed by structures within the subject;
  (c) extending the delivery cannula through the opening at the distal portion of the guide cannula along a first extension path to the selected site in the subject; and
  (d) releasing the therapeutic agent from the delivery cannula at the selected site in the subject to form an injection site.

17. The method of claim 16, further comprising, after the step of releasing the therapeutic agent at the selected site, the steps of:
  (e) retracting the delivery cannula a predetermined distance from the injection site; and
  (f) releasing the therapeutic agent from the delivery cannula at a second selected site in the subject to form a second injection site.

18. The method of claim 16, wherein the delivery cannula tapers from a proximal end to a distal end to form a tube having a diameter at its distal end which is smaller than the diameter at its proximal end.

19. The method of claim 16, further comprising, after the step of releasing the therapeutic agent at the selected site, the steps of:
  e) retracting the delivery cannula such that a distal end of the delivery cannula does not extend beyond the opening at the distal portion of the guide cannula;
  f) rotating the guide cannula a predetermined angle from the first extension path of the delivery cannula;
  g) extending the delivery cannula through the opening at the distal portion of the guide cannula along a second extension path to a second selected site in the subject; and
  h) releasing the therapeutic agent from the delivery cannula at the second selected site in the subject to form a second injection site.

20. The system of claim 1, wherein the delivery cannula is manufactured of a material selected from the group consisting of glass, a polymeric material, and a metal.

21. The system of claim 1, wherein the delivery cannula is manufactured from glass.

22. The system of claim 21, wherein the glass is borosilicate glass.

23. The system of claim 1, wherein the guide cannula is manufactured from a metal.

24. The system of claim 10, wherein the delivery cannula tapers from a proximal end to a distal end to form a tube having a diameter at its distal end which is at least ten fold smaller than the diameter at its proximal end.

25. The system of claim 10, wherein the guide cannula is manufactured from a metal.

26. The system of claim 10, wherein the delivery cannula tapers over a distance of about 4 centimeters.

27. A system for delivering a therapeutic agent to a selected site in a subject, comprising:
  a rigid guide cannula for penetrating the subject to a site adjacent to the selected site, the guide cannula having an axial bore extending therethrough within which a delivery cannula can be disposed, an open proximal end, an opening at a distal portion thereof, a distal end which is a blunt end, and a wall which is sufficiently rigid such that it is capable of imposing a predetermined trajectory on a delivery cannula disposed therein as the delivery cannula is extended through the opening at the distal portion of the guide cannula; and a delivery cannula disposable within the guide cannula for delivering the therapeutic agent to the selected site in the subject, the delivery cannula having an axial bore extending therethrough, a flexible distal end portion, and an outer diameter which is less than the bore diameter of the guide cannula, wherein the delivery cannula, when extended through the opening at the distal portion of the guide cannula at a predetermined trajectory imposed by the guide cannula, is capable of maintaining the trajectory within the selected site in the subject without being diverted by forces imposed by structures within the subject.

28. A system for delivering a therapeutic agent to a selected site in a subject, comprising:

a rigid guide cannula for penetrating the subject to a site adjacent to the selected site, the guide cannula having an axial bore extending therethrough, an open proximal end, an opening at a distal portion thereof, and a distal end which is a blunt end; and a delivery cannula disposable within the guide cannula for delivering the therapeutic agent to the subject, the delivery cannula having an axial bore extending therethrough, a flexible distal end portion, and an outer diameter at its distal most end which ranges from 1 micron to 700 microns.

29. The system of claim 28, wherein the outer diameter of the distal most portion of the delivery cannula ranges from 10 microns to 200 microns.

30. The method of claim 16, wherein the therapeutic agent comprises neural cells and the selected site of the subject comprises a site in the central nervous system.

31. A method for delivering a therapeutic agent to a selected site in a subject, comprising:

(a) inserting a rigid guide cannula adjacent to a selected site in the subject, the guide cannula having an axial bore extending therethrough within which a delivery cannula can be disposed, an open proximal end, an opening at a distal portion thereof, a distal end which is a blunt end, and a wall which is sufficiently rigid such that it is capable of imposing a predetermined trajectory on a delivery cannula disposed therein as the delivery cannula is extended through the opening at the distal portion of the guide cannula;

(b) inserting a delivery cannula into the guide cannula proximal to the opening at the distal portion, the delivery cannula releasably holding the therapeutic agent and having a flexible distal end portion and an outer diameter which is less than the bore diameter of the guide cannula, wherein the delivery cannula, when extended through the opening at the distal portion of the guide cannula at a predetermined trajectory imposed by the guide cannula, is capable of maintaining the trajectory within the selected site in the subject without being diverted by forces imposed by structures within the subject;

(c) extending the delivery cannula through the opening at the distal portion of the guide cannula along a first extension path to the selected site in the subject; and (d) releasing the therapeutic agent from the delivery cannula at the selected site in the subject to form an injection site.

32. A method for delivering a therapeutic agent to a selected site in a subject, comprising:

(a) inserting a rigid guide cannula adjacent to a selected site in the subject, the guide cannula having an axial bore extending therethrough within which a delivery cannula can be disposed, an open proximal end, an opening at a distal portion thereof, a distal end which is a blunt end, and a wall which is sufficiently rigid such that it is capable of deflecting, at a predetermined deflection angle relative to the midline of the guide cannula, a delivery cannula disposed therein as the delivery cannula is extended through the opening at the distal portion of the guide cannula; the guide cannula further having disposed within its bore a delivery cannula releasably holding the therapeutic agent and having a flexible distal end portion and an outer diameter which is less than the bore diameter of the guide cannula, wherein the delivery cannula, when extended through the opening at the distal portion of the guide cannula, is adapted to be deflected by a wall of the guide cannula at a predetermined deflection angle relative to the midline of the guide cannula and along a new trajectory imposed by the deflection angle and thereafter maintaining the new trajectory in the subject without being diverted by forces imposed by structures within the subject;

(b) extending the delivery cannula through the opening at the distal portion of the guide cannula along a first extension path to the selected site in the subject; and (c) releasing the therapeutic agent from the delivery cannula at the selected site in the subject to form an injection site.

33. A method for delivering a therapeutic agent to a selected site in a subject, comprising:

(a) inserting a rigid guide cannula adjacent to a selected site in the subject, the guide cannula having an axial bore extending therethrough within which a delivery cannula can be disposed, an open proximal end, an opening at a distal portion thereof, a distal end which is a blunt end, and a wall which is sufficiently rigid such that it is capable of imposing a predetermined trajectory on a delivery cannula disposed therein as the delivery cannula is extended through the opening at the distal portion of the guide cannula; the guide cannula further having disposed within its bore a delivery cannula releasably holding the therapeutic agent and having a flexible distal end portion and an outer diameter which is less than the bore diameter of the guide cannula, wherein the delivery cannula, when extended through the opening at the distal portion of the guide cannula at a predetermined trajectory imposed by the guide cannula, is capable of maintaining the trajectory within the selected site in the subject without being diverted by forces imposed by structures within the subject;

(b) extending the delivery cannula through the opening at the distal portion of the guide cannula along a first extension path to the selected site in the subject; and (c) releasing the therapeutic agent from the delivery cannula at the selected site in the subject to form an injection site.

34. A system for delivering a therapeutic agent to a selected central nervous system site in a subject, comprising:
a therapeutic agent comprising cells;

a guide cannula for penetrating the subject to a site adjacent to the selected site, the guide cannula having an axial bore extending therethrough within which a delivery cannula can be disposed, an open proximal end, an opening at a distal portion thereof, and a wall which is sufficiently rigid such that it is capable of deflecting, at a predetermined deflection angle relative to the midline of the guide cannula, a delivery cannula disposed therein as the delivery cannula is extended through the opening at the distal portion of the guide cannula; and a delivery cannula disposable within the guide cannula for delivering the therapeutic agent to the selected site in the subject, the delivery cannula having an axial bore extending therethrough, a flexible distal end portion, and an outer diameter which is less than the bore diameter of the guide cannula, wherein the delivery cannula, when extended through the opening at the distal portion of the guide cannula, is adapted to be deflected by a wall of the guide cannula at a predetermined deflection angle relative to the midline of the guide cannula and along a new trajectory imposed by the deflection angle and thereafter maintaining the new trajectory in the subject without being diverted by forces imposed by structures within the subject.

* * * * *